US010987031B2

(12) United States Patent
Pislak et al.

(10) Patent No.: US 10,987,031 B2
(45) Date of Patent: Apr. 27, 2021

(54) METHOD OF PERFORMING REAL EAR MEASUREMENTS BY PLACING A PROBE ELEMENT AT AN INTENDED POSITION FROM A TYMPANIC MEMBRANE OF AN INDIVIDUAL'S EAR CANAL AND A MEASURING SYSTEM CONFIGURED TO CARRY OUT SUCH METHOD (71) Applicant: SONOVA AG, Staefa (CH)

(72) Inventors: Stefan Pislak, Staefa (CH); Alfred Stirnemann, Zollikon (CH); Michael Boretzki, Ruti (CH); Manfred Duerst, Uster (CH); Harald Krueger, Affoltern a. A. (CH); Ullrich Sigwanz, Hombrechtigkon (CH); Martina Schuepbach-Wolf, Staefa (CH)

(73) Assignee: Sonova AG, Staefa (CH)

( * ) Notice: Subject to any disclaimer, the term of this patent is extended or adjusted under 35 U.S.C. 154(b) by 251 days.

(21) Appl. No.: 16/076,695

(22) PCT Filed: Feb. 9, 2016

(86) PCT No.: PCT/EP2016/052693
§ 371 (c)(1),
(2) Date: Aug. 8, 2018

(87) PCT Pub. No.: WO2017/137071
PCT Pub. Date: Aug. 17, 2017

(65) Prior Publication Data
US 2019/0046089 A1 Feb. 14, 2019

(51) Int. Cl.
*A61B 5/12* (2006.01)
*H04R 25/00* (2006.01)
(Continued)

(52) U.S. Cl.
CPC ............ *A61B 5/125* (2013.01); *A61B 5/1076* (2013.01); *A61B 5/12* (2013.01); *H04R 1/406* (2013.01);
(Continued)

(58) Field of Classification Search
CPC ............ A61B 5/125; A61B 5/126; A61B 5/12
See application file for complete search history.

(56) References Cited

U.S. PATENT DOCUMENTS 4,809,708 A * 3/1989 Geisler ................. A61B 5/121
600/552
4,813,430 A 3/1989 Hecox et al.
(Continued)

OTHER PUBLICATIONS

International Search Report received in PCT Patent Application No. PCT/EP2016/052693, dated Nov. 10, 2016.
(Continued)

*Primary Examiner* — Matthew G Marini
(74) *Attorney, Agent, or Firm* — ALG Intellectual Property, LLC (57) ABSTRACT A method of performing real ear measurements by a measuring system is described herein. The measuring system comprises a probe element adapted to be inserted in the ear canal of an individual; a loudspeaker configured to deliver a sample sound signal to the ear canal; at least one microphone configured to detect a response to the sample sound signal, wherein the probe element is in acoustic communication with the loudspeaker and cooperates with the at least one microphone; and a signal processing unit for performing an acoustic measurement of a response to the sample sound signal, based on an electrical input signal from the microphone.

16 Claims, 4 Drawing Sheets (51) Int. Cl.
*A61B 5/107* (2006.01)
*H04R 1/40* (2006.01)
*H04R 3/00* (2006.01)
*H04R 29/00* (2006.01)

(52) U.S. Cl.
CPC ............ *H04R 3/005* (2013.01); *H04R 25/70* (2013.01); *H04R 29/001* (2013.01)

(56) References Cited

U.S. PATENT DOCUMENTS

| | | | |
|---|---|---|---|
| 5,785,661 A | | 7/1998 | Shennib |
| 6,134,329 A | * | 10/2000 | Gao ..................... H04R 25/453 381/312 |
| 2009/0259461 A1 | * | 10/2009 | Arakawa ............... G10L 15/065 704/225 |
| 2010/0026034 A1 | | 2/2010 | Storgato et al. |
| 2014/0114209 A1 | * | 4/2014 | Lodwig .................. A61B 5/125 600/559 |
| 2016/0100259 A1 | * | 4/2016 | Guo ....................... H04R 25/30 381/60 |

OTHER PUBLICATIONS

Chan, et al.,Estimation of Eardrum Acoustic Pressure and of Ear Canal Length From Remote Points in the Canal, The Journal of the Acoustical Society of America, American Institute of Physics for the Acoustical Society of America, New York, NY, vol. 87, No. 3, Mar. 1, 1990, pp. 1237-1247.

Gerling I J, et al.,Comparison of Probe Tube Placement Methods in Real Ear Measurements, Hearing Instruments, Harcourt Brace Jovanovich Publ. Duluth, Minnesota, vol. 42, No. 3. Mar. 1, 1991, p. 20, 22.

* cited by examiner

METHOD OF PERFORMING REAL EAR MEASUREMENTS BY PLACING A PROBE ELEMENT AT AN INTENDED POSITION FROM A TYMPANIC MEMBRANE OF AN INDIVIDUAL'S EAR CANAL AND A MEASURING SYSTEM CONFIGURED TO CARRY OUT SUCH METHOD

The present invention relates to a method for performing real ear measurements by use of a measuring system comprising a sensing device adapted to be inserted in the ear canal of an individual, such as a probe element-microphone assembly or similar, particularly to a method designed to achieve a safe and correct placement of such sensing device in an individual's ear canal. The present invention also relates to a real ear measuring system configured to carry out the above method.

The present invention relates to the technical field of fitting hearing aids, or hearing devices, and allows to more comfortably and reliably optimize and/or verify the fitting of a given hearing aid to the individual characteristics of a hearing aid user's ear canal and tympanic membrane.

The term hearing aid shall be understood as a device to be worn at the vicinity or directly within the ear of a person to improve the individual hearing capacity of this person. Such an improvement may include the prevention of the receiving of certain acoustic signals in terms of ear protection.

In relation to their application and user indication, and according to the corresponding main solutions available on the market, such hearing devices can be worn, for instance, behind the ear (BTE), within the ear (ITE) or completely within the ear (CIC). The latest design developments have made available hearing devices that are even smaller than completely within the ear (CIC) devices, aptly named invisible in the canal (IIC) hearing aids.

Hearing aids normally comprise at least one microphone as electroacoustic input transducer; at least one speaker—usually called receiver—as electroacoustic output transducer; and an electronic signal processing circuitry, connected with said microphone and said speaker, for the processing and manipulation of electronic signals. This electronic signal processing circuitry may comprise analogue or digital signal processing devices. Said elements are usually arranged within at least one main case or shell of the hearing device. The electronic signal processing circuit performs various signal processing functions. Such signal processing functions can include amplification, background noise reduction, tone control, etc.

The signal processing functions of current hearing aids can be provided with the option of adjustable operational modes or parameters or characteristics, thus allowing user customization of the hearing aids or their prompt adaptive response to given, changeable environment conditions.

It will be recognized that the features of the present invention are substantially compatible with the fitting of any style of hearing aids.

Real ear measurements (REM), e.g. RECD-measurements or OEG measurements, are carried out for optimizing and/or verifying a fitting. In order to obtain precise and reliable indications which represent the actual characteristics of the individual's ear canal, it is necessary to place a sensing device, such as a probe element, in the proximity of the eardrum. The eardrum can also be called tympanic membrane. Generally the probe element takes the form of a probe tube which extends between an open tip end, adapted to be introduced in the ear canal, and an opposite end connected to a microphone. The probe tube thus lets an acoustical communication be stablished between the ear canal of a patient and the microphone.

For instance, real-ear-to-coupler difference (RECD) could be measured via a sensing device, typically in the form of a probe tube, that is measuring the difference between the output in the real-ear and the output on a 2 cc coupler that is used in the hearing aid fitting and verification process.

Real-ear-to-coupler difference (RECD) can be defined as the difference in decibels across frequencies between the sound pressure level (SPL) measured in the real ear canal and that, instead, in a 2 cc coupler, produced by a transducer generating the same output signal.

Generally, the RECD measurement procedure consists of two measurements: a first measurement in the form of a 2 cc coupler-based measurement; and a second measurement in the form of a real-ear measurement.

On the one hand, a 2 cc coupler measurement is made on the same coupler traditionally used for hearing aid fitting and verification. A transducer, such as a loudspeaker, from a real-ear measurement system delivers a signal into the 2 cc coupler and the system defines the sound pressure level (SPL) of the signal as a function of frequency.

The same signal is then delivered from the same transducer into the individual's ear, typically via the same sensing system, such as the abovementioned probe tube, which picks up the ear canal response to such signal. The real-ear system again measures the level of the signal, in this instance directly in the individual's ear, as a function of frequency.

Achieving a placement of a probe element at a target position from a tympanic membrane of an individual's ear canal which is suitable for performing real ear measurements is paramount. A target position of not more than 4 millimeters from the tympanic membrane is ideal for such purpose; otherwise a position of up to 6 millimeters from the tympanic membrane is also acceptable. A positioning of a probe element further away from the tympanic membrane than the above amounts leads to measurements errors.

However, if an operator was to push a probe tube into the ear canal of a patient needing to have his hearing aid customized without any guidance, such procedure would not only cause understandable unease and discomfort in the patient, but it could also prove dangerous for the patient. The condition that the tympanic membranes is never touched must be complied with, for the safety of a patient.

Currently, it is a general practice among most acousticians to avoid in the first place taking any measurements of insertion depths of a probe tube in an ear canal and to proceed, instead, by visual inspection through an otoscope. A tentative approach exists consisting in carefully pushing in a probe tube by random push-in distances until the patients signals pain when the eardrum is hit. U.S. Pat. No. 4,813,430 describes a non-automated process which implies the probe tube contacting the ear drum.

It is also known to determine the distance between probe-tube and eardrum by taking into account a notch in a spectrum sensed at a probe-tube opening. Generally, in fact, a notch, or dip, is observable in the spectrum of a sound signal at the frequency "lambda/4". A certain correlation between notch-frequencies and ear-drum distances can be established. According to this method, an acoustician would still need to watch the spectrum, interpret the situation and, based on his educated guess, stop pushing the tube before it hits the eardrum. A use of such "quarter wavelength dip" to infer a distance from a tympanic membrane is disclosed in EP 0 326 611.

Such a solution brings about several drawbacks, a major one being that the acoustician, or in general the operator, must direct his attention to the patient and, concurrently, to a display showing a spectrum. Moreover, the spectral information still needs to be interpreted and translated into usable distance information, which requires experience and makes the overall procedure approximate and risky.

Thus, there exists a need for an method of performing real ear measurements by a measuring system that achieves a placement of a probe element at a target position from a tympanic membrane of an individual's ear canal suitable for performing real ear measurements, as well as for a correlated measuring system, which is designed in a way that:

no special initial setting needs to be assumed and artificially recreated;

insertion of the probe element is carried out in a controlled way, taking into account the situation within the ear canal;

the insertion and placement procedure of a probe element in the ear canal is continuous and adaptive, the collection of data relative to the ear canal in order to estimate a prediction distance from the tympanic membrane not stopping during adjustment and repositioning of said probe element;

safety is guaranteed, even when manipulation of the probe element during insertion in the ear-canal is carried out by operators or clinicians with limited experience; and no specific background knowledge of operators is required, the process being guided by the execution of an algorithm which automatically provides the operator with an indication of a safe correction distance by which the position of a probe element needs to be adjusted.

Accordingly, a major objective of the present invention is to provide an innovative approach to guiding an operator to a safe and effective placement of a probe element in the ear canal of a patient at a target position, in order to carry out reliable and precise real ear measurements.

Another objective of the present invention is to relieve an operator, such as an audiologist, a clinician or an assistant, from having to apply specific knowledge and from making educated guesses while placing a probe element in the ear canal for the purpose of real ear measurements. A distracting monitoring and interpretation by the operator of complex data, such as spectra information, is avoided when applying the method according to the present invention, which provides instead the operator with clear and immediate instructions and/or feedback on the correction, or push-in, distances which progressively can be safely applied to reach a target position of the probe element.

Yet another objective of the present invention is to consider the reliability of the data continuously collected and measured by the probe element itself. Based on such data, in fact, a subsequent assessment of a prediction distance from the tympanic membrane would be done. The present method allows quantifying the reliability that the ensuing calculations, to estimate a prediction distance and ultimately a correction distance, would yield trustworthy results. The above calculations of predicted distance are performed by the algorithm underlying the present invention only once it has been established that sample sound signals (emitted in the ear canal by way of said probe element or otherwise) are representative of an actual situation in the ear canal. Otherwise, the emission of further sample sound signals will continue, for a new analysis thereof.

These problems are solved through a method of performing real ear measurements, and a correlated measurement system configured to carry out such method, according to the main claims. Dependent claims further introduce particularly advantageous embodiments for such a method and related system.

The inventive solution basically requires estimating, by spectra measurement, a prediction distance of a probe element from a tympanic membrane; and only if such prediction distance is less than a threshold value, providing the information that the probe element is at a target position and performing a real ear measurement; otherwise, determining a correction distance, as a function of the prediction distance, by which an adjustment of the position of the probe element is instructed. The process, which is iterative and adaptive, continues until it is estimated, by specific calculations, that a residual distance of the probe element from the tympanic membrane is suitable to performing real ear measurements.

Advantageously, the present invention carries out the calculations relative to the abovementioned prediction distance, and the correlated correction distance, only when it is useful, in that it is assessed that a high degree of reliability can be attributed to the measurements. Acoustic or mechanical disturbances in the process are identified and accounted for, using a series of sample sound signals.

Moreover, in a situation where it is virtually impossible to know with an absolute degree of certainty where an operator has positioned a probe element within an ear canal, the present invention effectively offers an optimal solution to providing the most likely position of such probe element relative to the tympanic membrane. This is obtained by using probability distributions that a probe element is positioned over a range of distance values within the ear canal, wherein predefined distance values within a given distance range may be provided.

Other objectives, features and advantages of the present invention will be now described in greater detail with reference to specific embodiments represented in the attached drawings, wherein.

Figure 1:
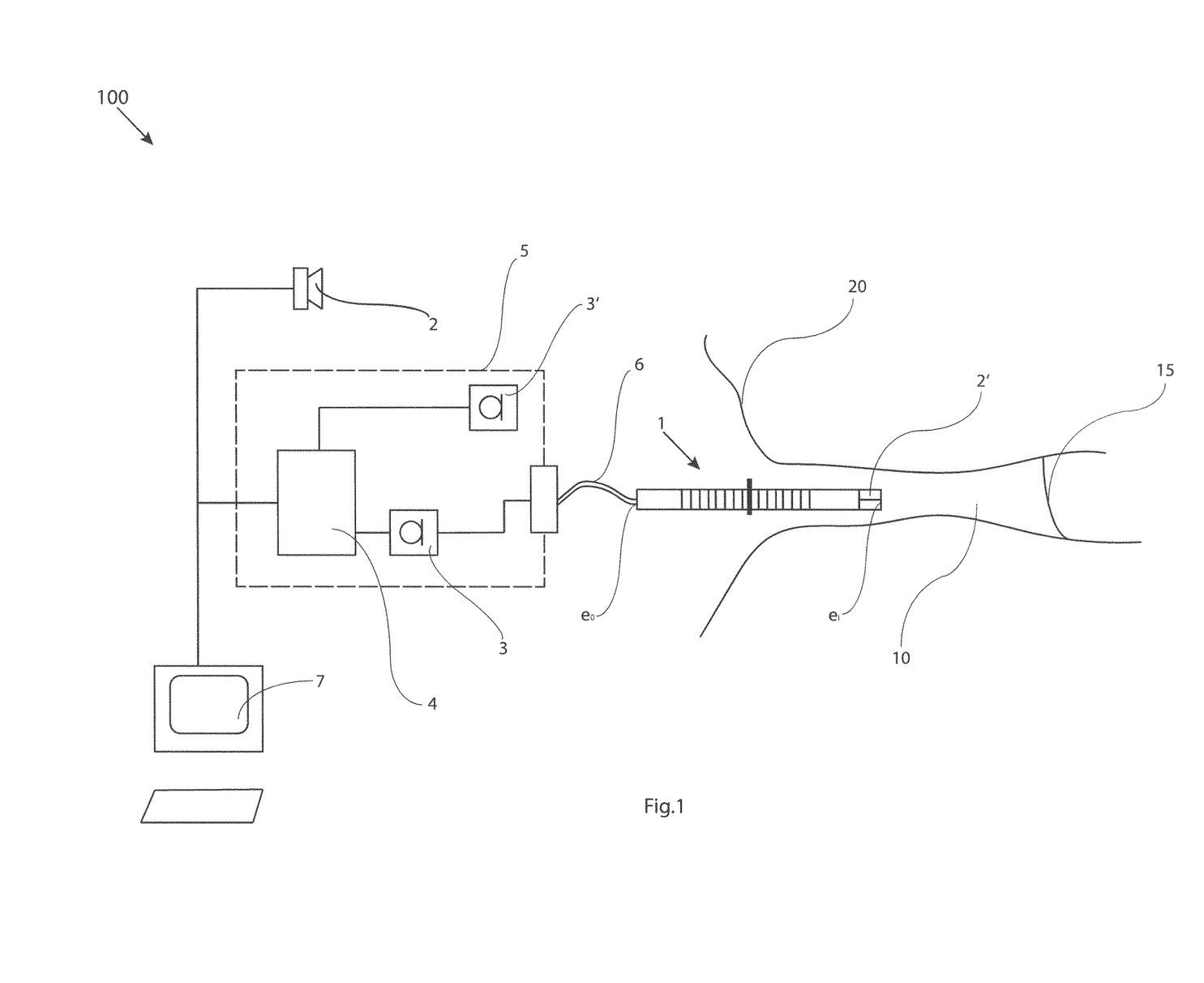
FIG. 1 is a schematic representation of a possible embodiment for a measuring system, designed to work according to the work-flow of the present invention.

With reference initially to the exemplifying embodiment of FIG. 1, a measuring system 100 configured to carry out the process according to the present invention comprises a probe element 1 adapted to be inserted in the ear canal 10 of an individual. Such a probe element 1 can take the form of a probe tube, as typically employed in real ear measurements. Preferably, the probe element 1 comprises a scale as shown in FIG. 1, or is more in general calibrated to provide an operator with an indication of changes in the adjustment of the position of the probe element 1, for instance with respect to the exit 20 of the ear canal 10 at the concha.

A loudspeaker 2 is configured to deliver at least a sample sound signal to the ear canal 10. In FIG. 1, the loudspeaker 2 is external to the ear canal 10. At any rate, the probe element 1 is in acoustic communication with the loudspeaker 2. Other loudspeakers can be provided for the purpose of emitting sample sound signals aimed to the ear canal 10. By way of example, a loudspeaker 2' can be provided at a tip of the probe element 1, i.e. at an end $e_t$ of the probe element 1 to be oriented towards the tympanic membrane 15. A loudspeaker 2' is thus configured to be brought inside the ear canal by way of the probe element 1.

The measuring system 100 also comprises at least one microphone configured to detect a response to said at least one sample sound signal. Preferably, as shown in FIG. 1, the measuring system 100 comprises two microphones.

A first reference microphone 3' is positioned at a location, with respect to the anatomy of an individual for whom a hearing aid needs to be fitted, suitable for detecting the specific response to said sample sound signal.

The first reference microphone 3' can, for instance, be positioned at a cheek of such individual, or above an ear of the individual or lateral to the ear.

A second microphone 3 is preferably provided to cooperate with the probe element 1. Such second microphone 3 can, for instance, be coupled to an end e, of said probe element 1 to be oriented away from said tympanic membrane 15. In the embodiment of FIG. 1, microphone 3 is coupled with the probe element 1 in a way that the response to a sound signal coming back from a remaining volume between the probe element 1 and the tympanic membrane 15—for instance, through a signal transmission means 6 such as a sound tubing and/or an electrical audio cable—is picked up by the microphone 3. Microphone 3 can also be alternatively positioned, for instance directly at the tip of the probe element 1. The provision of two microphones 3, 3' as above introduced can be advantageous in that it ensures independency from sensitivity variations of the loudspeaker 2, 2'.

A signal processing unit 4 performs, by a dedicated measuring software, an acoustic measurement of a response to the sample sound signal, based on an electrical input signal from the microphone 3, 3'. In FIG. 1, the signal processing unit 4 and the microphones 3, 3' are comprised in a casing 5, which can be strapped, or otherwise fastened, onto an ear of an individual, so that the casing 5 lies for instance in the proximity of an individual's cheek.

The measuring software of the signal processing unit 4 can cooperate with modules of a fitting software, running for instance on a fitting computer system or fitting station 7, in order to implement an algorithm according to the present invention, aiming at achieving a placement of a probe element 1 at a target position $p_{target}$ from a tympanic membrane 15 of an individual's ear canal 10 which is suitable for ultimately performing real ear measurements.

Alternative configurations of the measuring system to the one exemplified in FIG. 1 are possible. For instance, at least part of the signal processing functionalities can be directly incorporated in the fitting computer system or fitting station 7. It is also possible to have more than one signal processing unit—operatively inter-connected with each other and cooperating with a fitting computer system or fitting station—differently positioned with respect to a casing comprising the microphones.

The method according to the present invention comprises a step of placing the probe element 1 at a trial distance from the tympanic membrane 15. With reference to the exemplifying illustrations of FIG. 2 and FIG. 3, such trial distance has been designated with the reference sign $d_{real}$.

Preferably, such preliminary placement is done in a way the probe element 1 comes to be in longitudinal alignment with, or proximal to, the ear canal 10. At this stage, the probe element can also be brought, at least partially, inside the ear canal 10. An operator can, for instance, preliminarily place the probe element 1 in a way that it extends approximately up to the first bend of the ear canal.

Preferably, the appropriate level of the sample sound signals has been preventively estimated. For this purpose, the measurement software can have measured the sound levels at the probe element 1 via microphone 3 and at the reference microphone 3' and provided the relative results to the fitting software for calculation of the sound level.

After placing the probe element 1 at a trial distance $d_{real}$, the method according to the present invention comprises the steps of emitting, by the loudspeaker 2, 2', at least a sample sound signal in the ear canal 10; detecting a response to said sample sound signal by the probe element 1 and measuring, by the signal processing unit 4, the spectrum of the sample sound signal.

The at least one sample sound signal is preferably measured at third octave levels, in a frequency range comprised between 0 Hz and 20 kHz, preferably between 125 Hz and 10 kHz. However, any other frequency resolution that is related to an octave is in principle usable. Analogously, any frequency range detectable by the reference microphone 3' and/or by the microphone 3 coupled to an end of a probe element can be employed.

It follows a step, to be preferably performed by a module of the fitting software but also implementable directly by the measuring software, of estimating a prediction distance, $d_{pred}$, of the probe element 1 from the tympanic membrane 15, based on the spectrum measurement above carried out.

Only if such prediction distance $d_{pred}$ is less than a first measuring distance threshold value, the method according to the present invention provides the information to an operator that the probe element 1 is at a target position, $p_{target}$, that is suitable for performing real ear measurements. Therefore, only under the above proximity condition that the probe element 1 is close enough to the tympanic membrane 15, the fitting software instructs an operator to conclude the positioning and adjustment process of the probe element 1 and to subsequently perform a real ear measurement. Alternatively, only under such a proximity condition the fitting software automatically executes a real ear measurement.

If not, that is if the above proximity condition is not met and the probe element 1 cannot be deemed to be at such a target position, $p_{target}$, the method according to the present invention comprises a step of determining a correction distance, $d_{corr}$, as a function of the prediction distance $d_{pred}$.

As a consequence, then, the fitting software instructs the adjustment, by an operator, of the position of the probe element 1 according to the indication of the correction distance $d_{corr}$, thus reaching a residual distance $d_{res}$ of the probe element 1 from the tympanic membrane 15.

The steps of emitting at least a sample sound signal; detecting a relative response by the probe element 1; measuring the spectrum corresponding to the sample sound signal; estimating a prediction distance $d_{pred}$ based on the measured spectrum and assessing whether such prediction distance $d_{pred}$ is less than a first measuring distance threshold value; are then repeated as above outlined.

Figure 2:
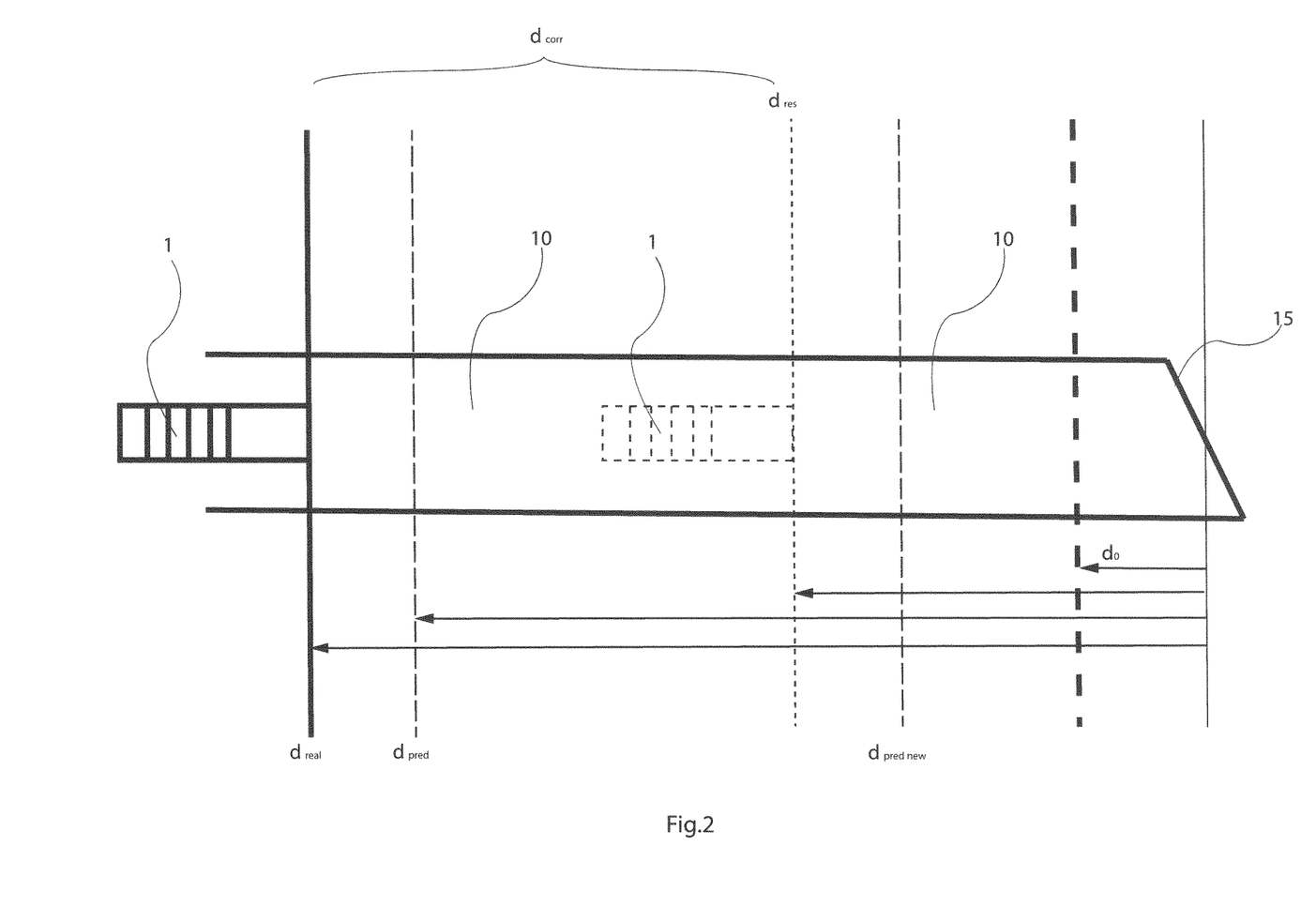
FIG. 2 is a schematic representation of some steps of an embodiment of the process according to the present invention, aimed at iteratively achieving a placement of a probe element at a target position from a tympanic membrane of an individual's ear canal, the target position being suitable for performing real ear measurements.

FIG. 2 shows a schematic exemplification of some of the abovementioned steps for an embodiment of the process according to the present invention, aimed at iteratively achieving a placement of a probe element at a target position from a tympanic membrane 15 suitable for performing real ear measurements. Specifically, in FIG. 2, two iterations of the process are shown, with respective calculations of two successive prediction distances for the tympanic membrane, $d_{pred}$ and $d_{pred\ new}$, in the adjustment process to reach an intended target position. The probe element 1 is initially positioned by an operator at a trial distance $d_{real}$ from the tympanic membrane. Based on analysis of emitted sample sound signals as explained, a corresponding prediction distance $d_{pred}$ is estimated. As the condition set that $d_{pred}$ be less than a first measuring distance threshold value is not met, the method derives, in function of such prediction distance $d_{pred}$ and/or of other variables, a correction distance $d_{corr}$.

Following an adjustment, by an operator, of the position of the probe element 1 according to the indication of such correction distance $d_{corr}$, the probe element 1 reaches a position at a residual distance $d_{res}$ from the tympanic membrane 15. At this stage, a corresponding, new prediction distance $d_{pred\ new}$ is estimated again and compared with said first measuring distance threshold value. In connection with the calculation of the correction distance $d_{corr}$, at least a safety threshold $d_0$ may be taken into account which is designed to prevent the probe element 1 from touching the tympanic membrane 15.

Figure 3:
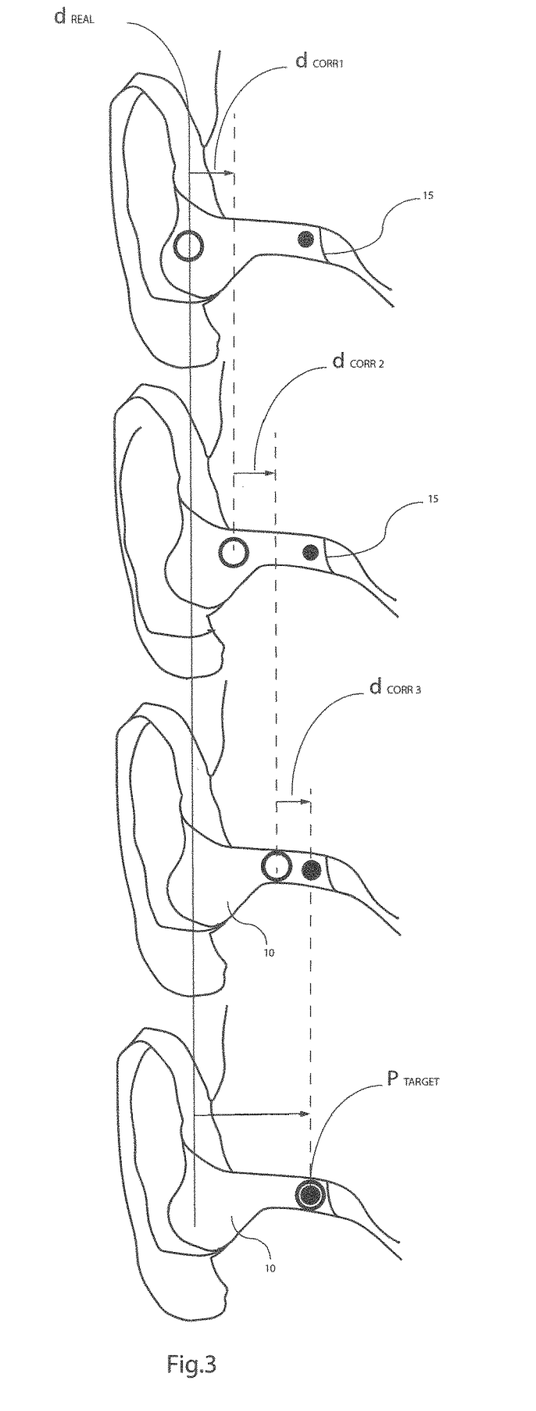
FIG. 3 is a schematic representation of an example of a sequence of steps according to the present invention, showing in succession three stages of an adjustment of the position of a probe element, by application of respective push-in distances, or correction distances, towards a target position for the probe element's tip.

In FIG. 3 it is schematically and synthetically represented a sequence of steps according to the present invention, showing in succession three stages of an adjustment of the position of a probe element, by application of respective correction distances $d_{corr1}$, $d_{corr2}$ and $d_{corr3}$ towards a target position for the probe element's tip. Following the successive indications of these three correction distances, corresponding to three different estimated prediction distances, the operator pushes the probe element in three times, before being provided with the indication that the target position has been reached.

The method according to the present invention can also comprise the steps of calculating, for an emitted sample sound signal, a respective gain, designatable as real ear probe element positioning gain (the acronym being REPTPG, when the probe element takes the form of a probe tube), wherein the gain results from the difference between a sound level measured by the microphone 3, coupled to an end $e_o$ of the probe element 1; and a sound level measured by the reference microphone 3', for instance at the cheek of the individual on whom the real ear measurement is to be made.

The method according to the present invention preferably comprises the step of sequentially emitting, and then sequentially measuring, a series of sample sound signals, whereby the signal processing unit 4 measures the spectrum of each of the sequential sample sound signals at given time intervals.

In practice, the loudspeaker preferably emits a continuous sound or noise, such as a continuous so-called white or pink sound (wherein a white sound normally has a flat frequency spectrum when plotted as a linear function of frequency, whereas the frequency spectrum of pink noise is linear in logarithmic space). Such a continuous sound can, however, be easily described as a series of sequential, discrete sample sound signals, each one of them spanning over a respective discrete time interval. Thus, the signal processing unit 4 can practically also come to measure an average of these several sample sound signals emitted over respective, discrete time intervals.

In the method according to the present invention, preferably a sample sound signal is collected and measured by the measuring software at about every 64 milliseconds, so that it takes 0.64 seconds to collect ten sample sound signals. As a consequence of that, at the above sampling rate, an operator can get every 0.64 seconds an information relating to the measurement.

The method according to the present invention preferably relies, for calculation of a prediction distance $d_{pred}$, on a weighted average of the real ear probe element positioning gains (also designated with the acronym REPTPG, as above pointed out) of the series of sample sound signals, for instance of successive 10 samples.

In formulas, if SampleID stands for one of the samples; f stands for frequency; and Weight(SampleID, f) stands for the product of a multiplicity of weighting factors, it can be synthetically stipulated that, for a given measured sample:

$$REPTPG(SampleID, f) = \\ LevelAtProbeTube(SampleID, f) - LevelAtReferenceMic(SampleID, f)$$

Then, a weighted average of the real ear probe element positioning gains, by way example across all of 10 SampleIDs, can get calculated as:

$$AverageREPTPG(f) = \\ \frac{\sum_{SampleID=1}^{10} (Weight(SampleID, f) * REPTPG(SampleID, f))}{\sum_{SampleID=1}^{10} (Weight(SampleID, f))}$$

Preferably, weighting factors are used for calculating the above weighted average which take into account at least one of the following variables:
- a time sequence of the series of sample sound signals, wherein a weighting factor is attributed based on the temporal position within the series of sample sound signals; and/or
- environmental disturbances, wherein sample sound signals affected by environmental disturbances are attributed proportionally lower weights; and/or
- manipulations of the probe element 1 by an operator, wherein sample sound signals affected by the manipulations are attributed proportionally lower weights.

Advantageously, the weight may increase proportionally to the proximity to a conclusion of the process of collecting and measuring the series of sample sound signals. Therefore, a higher weighting factor is attributed to a sample sound signal which is temporally close to the end of the collecting and measuring process.

Preferably, the environmental disturbances and/or manipulations are quantified based on deviations between an expected sound level at the reference microphone 3' and an actual sound level as measured by said reference microphone 3'.

Alternatively, the environmental disturbances and/or manipulations can be quantified based on deviations between an expected and a measured real ear probe element positioning gain (REPTPG), particularly for frequencies lower than 400 Hz. Yet again, the environmental disturbances can be quantified based on deviations between the real ear probe element positioning gain, or REPTPG, of a single sample sound signal and the average REPTPG of all sample sound signals.

Preferably, a reliability measure is provided as a function of said weighting factors. The steps of iteratively estimating a prediction distance $d_{pred}$ and, in case it is determined that it is necessary, adjusting by a correction distance $d_{corr}$ are only executed if such reliability measure provides a result for said series of sample sound signals which is above a reliability threshold value.

In case the reliability measure provides a result, for the given series of sample sound signals, which is below a reliability threshold value, the operator is provided with an information that an estimate of a prediction distance $d_{pred}$ of the probe element 1 from the tympanic membrane 15 will not be attempted based on said series of sample sound signals. Instead, the operator is presented with the information that the steps of emitting sample sound signals in the ear canal 10; detecting a response to the sample sound signals by the probe element 1 and measuring the spectrum of said sound signals will need to be repeated for a new series of sample sound signals.

The check, by the fitting software, that the calculated weighted average of the real ear probe element positioning gains, AverageREPTPG(f), is reliable is preferably performed based on the above introduced weighting factors and by comparing the resulting reliability value to a threshold value. If the obtained reliability is low, this likely entails that the operator is manipulating the probe element or that the signal from the speaker 2, 2' is disturbed by the environment.

With reference to the example made herein, an operator can get every 0.64 seconds an information relating to the ongoing measurement, wherein this information can be either:
that the measurement is not reliable; or
that the current position of the probe element has been estimated by deriving a prediction distance $d_{pred}$ and an adjustment by a correction distance $d_{corr}$, is suggested; or
that the probe element is positioned close enough to the tympanic membrane, so that it is deemed to be already at a target position $p_{target}$.

Provided that the above reliability conditions are met, the method according to the present invention estimates, by a spectrum measurement of the sample sound signals, a prediction distance $d_{pred}$ of the probe element 1 from the tympanic membrane 15.

In fact, attributing an absolute certainty to the determined value of a distance between a tip of a probe element and a tympanic membrane may prove a somewhat hazardous approach, because it is prone to mistakes.

Preferably, instead, the prediction distance $d_{pred}$ according to the present method is calculated based on a statistical probability distribution that the prediction distance $d_{pred}$ equals each one of a range of distance values from a tympanic membrane. In more specific embodiments, the prediction distance $d_{pred}$ according to the present method can be calculated based on a statistical probability distribution that that the prediction distance $d_{pred}$ equals each one of a range of predefined distance values from a tympanic membrane or, otherwise expressed, each one of a set of distance values comprised in a distance range from a tympanic membrane.

Taking into account the likelihood that the probe element 1 is positioned at a certain distance value may therefore represent a more realistic approach.

Figure 4:
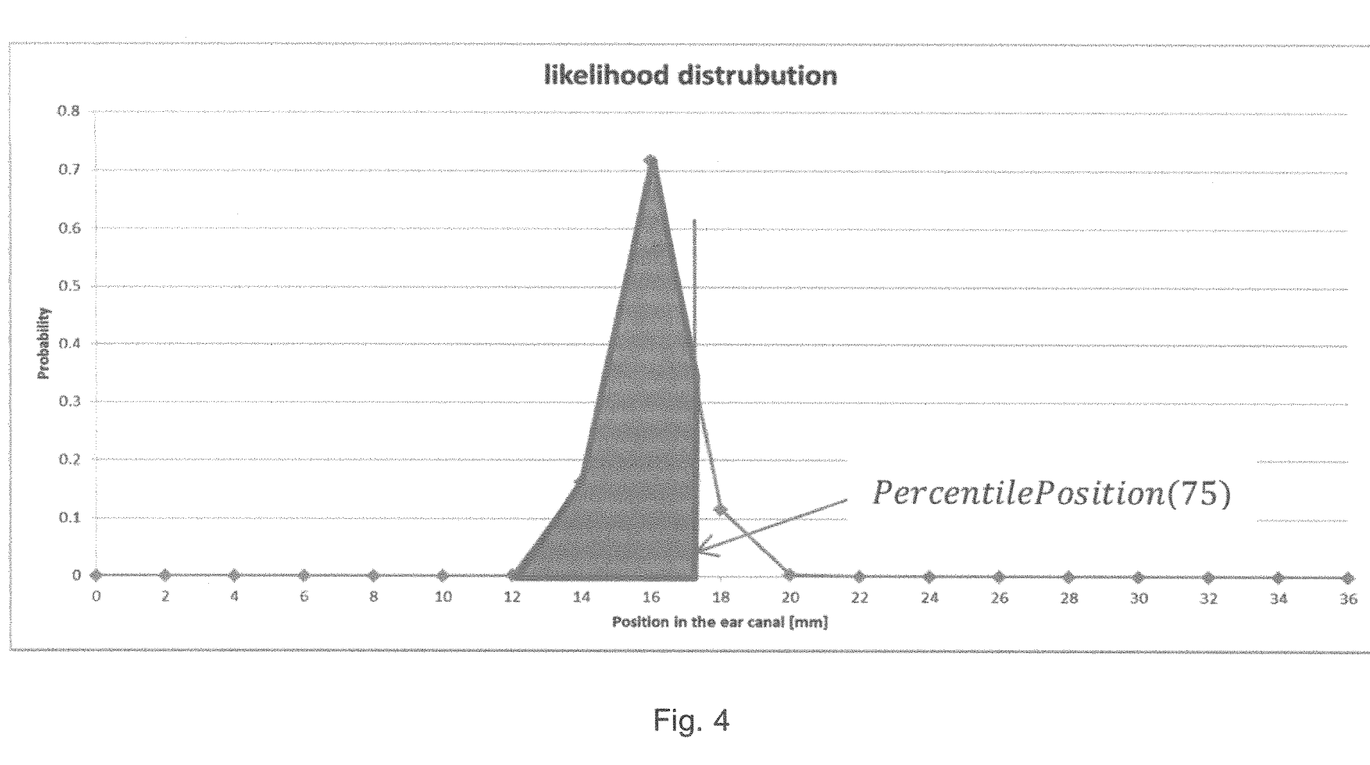
FIG. 4 is a diagram showing an example of a specific statistical probability distribution for estimating a prediction distance from a tympanic membrane, showing a probability that such prediction distance equals each one of a range of predefined distance values from a tympanic membrane.

By way of an example illustrative of a preferred (but not exclusive), statistical approach according to the present invention, in FIG. 4 it is represented a calculated probability that the probe element 1 is located at a certain position, out of a discrete number of possible distance values from the tympanic membrane. More specifically, in FIG. 4 such probability is estimated in connection of a set of 19 possible positions, having respective distances from the tympanic membrane 15, at intervals of 2 millimetres, for an overall stretch (i.e. distance range from the tympanic membrane) of 36 millimetres.

In the case of FIG. 4, the present invention is implemented based on the knowledge of the probability for each one of a discrete number of predefined distance values from the tympanic membrane 15, the predefined distance values being taken/selected within a certain distance range. Anyhow, the present invention can also be applied to cases where the probability distribution is continuous, such that the probability distribution is described by a probability density function. In these cases, the probability density continuously describes the relative likelihood for the prediction distance $d_{pred}$ to take on a given value comprised within a distance range from a tympanic membrane, wherein the probabilities associated to all of the values comprised in said distance range have been calculated and are known.

In the example of FIG. 4, the diagram shows how the probe element is with a probability of about 16% at 14 millimetres from the tympanic membrane; with a probability of about 72% at 16 millimetres; and with a probability of about 12% at 18 millimetres. All other potential probe element positions have a probability of 0%.

Preferably, the output of a statistical probability distribution that the prediction distance $d_{pred}$ equals each one of a range of distance values is based on a linear discriminant analysis model. Preferably, a probability is determined for a discrete number of predefined distance values from the tympanic membrane. However, a probability density can also be used, wherein the probability is known for every distance value comprised within a given distance range from the membrane.

Such linear discriminant analysis model comprises the step of applying a matrix of measured sample sound signal data, correlated to known probe element-tympanic membrane distances, to the measured characteristics of the emitted sample sound signals. In particular, preferably in the method according to the present invention the abovementioned matrix is applied to the real ear probe element positioning gain (REPTPG) of an emitted sample sound signal, as already introduced, in order to obtain a statistical probability distribution. In such an embodiment, the matrix of measured sample sound signal data, correlated to known probe element-tympanic membrane distances, can be derived by measuring the REPTPG for known probe element positions, for an array of different individual's ears.

Preferably, the prediction distance $d_{pred}$ is calculated as the weighted average of said predefined distance values, where the statistical probability distribution is used as the weight for each predefined distance value. The result of such an operation yields a prediction distance $d_{pred}$ which is effectively the most likely position occupied by the probe element 1 with respect to the tympanic membrane 15.

In the specific example of FIG. 4, where a number of 19 possible positions are considered, the above relations translate synthetically in a formula as follows:

$$dpred = \frac{\sum_{PTPID=1}^{19} ProbeTubePosition(PTPID) \cdot Probability(PTPID)}{\sum_{PTPID=1}^{19} Probability(PTPID)}$$

As already pointed out, only if the prediction distance $d_{pred}$ thus derived is less than a first measuring distance threshold value, the information is provided that the probe element 1 is at an intended target position $p_{target}$ and a real ear measurement is performed. In one preferred embodiment, it is advantageous to set a first measuring distance threshold value to 6 millimeters, therefore requiring that the $d_{pred}$ value above calculated is less than 6 millimeters:

dpred<6 mm.

In order to compensate for a distortion effect introduced in the above formula especially by probability distributions more dispersed than the relatively clustered distribution shown in FIG. 4, the method according to the present invention preferably also introduces the calculation of a percentile of the statistical probability distribution, to determine that the result is below a second measuring distance threshold value. In this respect, the shaded area of FIG. 4 represents the $75^{th}$ percentile, that is the distance value below which there is a 75% chance that the probe element is located.

This second measuring distance threshold value, correlated to a percentile, and preferably to the 75th percentile, duly takes into account situations wherein there exists a significant probability for the probe element to be positioned at predefined distance values which are far away from each other, over a larger stretch.

Additionally to the condition that $d_{pred}$ be less than a first measuring distance threshold value, such a further percentile condition can be set as necessary for the software to provide the information that the probe element is at an intended target position $p_{target}$.

In one preferred embodiment, it is advantageous to set said second measuring distance threshold value to 8 millimeters, therefore requiring that the $75^{th}$ percentile value above discussed is less than 8 millimeters:

PercentilePosition(75)<8 mm

Alternatively, the method according to the present invention can be adjusted to take into account either of the abovementioned conditions, thus requiring that either of the related measuring distance threshold values be respected.

In the example of FIG. 4 none of the criteria given above is met, which implies that the iteration according to the present method would continue by determining a correction distance $d_{corr}$, as a function of the prediction distance $d_{pred}$, and by instructing the adjustment of the position of the probe element 1 according to the indication of such correction distance $d_{corr}$.

Preferably, the correction distance $d_{corr}$ is calculated on the basis not only of the prediction distance $d_{pred}$, but also of the statistical probability distribution and of at least one safety threshold designed to prevent the probe element 1 from contacting the tympanic membrane 15.

In a possible embodiment, a first safety threshold $d_0$ can equal the prediction distance $d_{pred}$ subtracted by a set value.

In addition to that, or alternatively to that, a second safety threshold can be used which is defined as a pre-set maximum adjustment value for the probe element. For instance, it can be preventively set that an operator should never be instructed to adjust the position of a probe element by more than 20 millimetres.

In a particular embodiment, the correction distance $d_{corr}$ can be a function of:
the abovementioned first safety threshold $d_0$,
said preset maximum adjustment value for the probe element; and
push-in distances based on percentiles of the statistical probability distribution and/or positive push-in distances designed to keep the process of adjustment of the probe element progressing.

In a more specific embodiment, the correction distance $d_{corr}$ can be the minimum between:
the abovementioned first safety threshold $d_0$,
said preset maximum adjustment value for the probe element; and
the maximum between push-in distances based on percentiles of the statistical probability distribution and/or positive push-in distances designed to keep the process of adjustment of the probe element progressing.

The method according to the present invention can comprise the step of providing a feedback to an operator relating to the correction distance $d_{corr}$ and/or to the reaching of the target position $p_{target}$, in order to allow an adjustment of the position of the probe element 1 according to the indication of such correction distance $d_{corr}$ and/or to give the feel of how close the operator is to attain the target position $p_{target}$.

Such feedback can be tactile and/or acoustic and/or visual.

In case of visual feedback, as it is represented in FIG. 3, a graphic indication can be preferably provided to the operator of how large a push-in action can be to move the probe element towards a tympanic membrane, when applying a correction distance $d_{corr}$.

The display of push-in distances, or correction distances $d_{corr}$, can be enriched with additional information, for instance about the reliability of the displayed values. The scale on the probe element 1 can thus also help relate a displayed correction distance $d_{corr}$ with a current position of the probe element 1 within an ear canal 10.

Alternatively, an acoustic signal, namely an iterative or pulsed beep, may be used to provide an operator with a feedback, wherein the beep interval is shortened as the tube approaches the eardrum. A more continuous beep is presented as the probe element gets increasingly closer to a target position $p_{target}$.

Preferably, the beep has a frequency in the lower frequency range, while the upper frequency range is left unobstructed such that there is no interference with the process of estimating a prediction distance $d_{pred}$. Various properties of such acoustic signal or beep may be modulated to correlate to the residual distance $d_{res}$ from the tympanic membrane, for example the pitch, the number of simultaneous sounds, the pitch-interval between two sounds, the pause between two beeps, the length of the beeps etc. The acoustic signal may also be a speech output, for example a number indicating a length in millimeters by which the operator needs to advance with the probe element towards a tympanic membrane.

A feedback to an operator on the status of a process of placement of a probe element 1 at a target position $p_{target}$ from a tympanic membrane 15 of an individual's ear canal 10 can also have a tactile form. A corresponding feedback signal can be transmitted, for instance, via a vibration. Such a vibration can be implemented using an application running on a smartphone—or on an analogous device, also wearable—carried by the operator. The fitting computer system or fitting station 7 can thus cooperate with the smartphone so that the above feedback can be notified to the operator, for instance by WLAN or Bluetooth. A feedback signal can also be provided by a flashing LED integrated in a component of the measuring system adapted to implement the method according to the present invention. The LED can be integrated, for instance, in a neck-worn component of the measuring system or directly on the body of the probe element. The flashing may be modulated like the above described beep signal.

Once the probe element 1 has been brought to the target position $p_{target}$ from a tympanic membrane 15 of an individual's ear canal 10 suitable for performing real ear measurements, the fact that a successful placement of the probe element 1 has been achieved can be confirmed by an operator, for instance by a push button on a component of the measuring system. Alternatively, the successful placement may also be detected automatically, for instance based on the fact that the estimated distance from the tympanic membrane remains constant and within a target range for a certain time. The real ear measurement may then start automatically. There may also be a "count-down" until the start of the measurement. In this case, the operator may be given the chance to cancel the measurement by simply pulling the probe element out of the target range.

The invention claimed is:

1. A method of performing real ear measurements by a measuring system,
the measuring system comprising:
a probe element adapted to be inserted in an ear canal of an individual;
a loudspeaker configured to deliver a sample sound signal to the ear canal;
at least one microphone configured to detect a response to the sample sound signal;
wherein the probe element is in acoustic communication with the loudspeaker and cooperates with the at least one microphone; and
a signal processing unit for performing an acoustic measurement of a response to the sample sound signal, based on an electrical input signal from the at least one microphone,
the method aiming at preventing the probe element from contacting a tympanic membrane of the ear canal of the individual while achieving a placement of the probe element at a target position from the tympanic membrane which is suitable for performing real ear measurements, and the method comprising the steps of:
a) placing the probe element at a trial distance from the tympanic membrane;
b) emitting, by the loudspeaker, at least the sample sound signal in the ear canal, detecting a response to the sample sound signal by the probe element and measuring, by the signal processing unit, a spectrum of the sample sound signal;
c) determining, by the measurement system, a statistical probability distribution that a current distance of the probe element equals each one of a range of distance values from the tympanic membrane;
d) estimating, by the measurement system based on the measurement of the spectrum and the statistical probability distribution, a prediction distance of the probe element from the tympanic membrane;
e) determining, by the measurement system, whether the prediction distance is less than a first measuring distance threshold value;
f) only if the prediction distance is less than the first measuring distance threshold value, providing, by the measurement system, information to an operator that the probe element is at the target position and performing a real ear measurement;
g) if the prediction distance is not less than the first measuring distance threshold value, determining, by the measurement system, a correction distance as a function of the prediction distance;
h) instructing, by the measurement system, the operator to adjust a position of the probe element based on the correction distance, thus reaching a residual distance of the probe element from the tympanic membrane; and
i) repeating steps b) to i) until the prediction distance is less than the first measuring distance threshold value.

2. The method of claim 1, wherein the statistical probability distribution indicates the likelihood that the prediction distance equals each one of a range of predefined distance values from the tympanic membrane.

3. The method of claim 1, wherein:
the at least one microphone includes a first reference microphone and a second microphone;
the first reference microphone is provided at a location that is positioned with respect to the individual and that is suitable for detecting the response to the sample sound signal; and
the second microphone is coupled to an end of the probe element.

4. The method of claim 3, further comprising calculating, for an emitted sample sound signal, a respective gain, designatable as real ear probe element positioning gain, wherein the gain results from a difference between a sound level measured by the second microphone at the end of the probe element and a sound level measured by the first reference microphone.

5. The method of claim 4, wherein at step b) a series of sample sound signals are sequentially emitted and measured, whereby the signal processing unit measures the spectrum of each of the sequential sample sound signals at given time intervals.

6. The method of claim 5, wherein the spectrum of a sample sound signal is collected and measured at about every 64 milliseconds.

7. The method of claim 6, further comprising calculating a weighted average of the real ear probe element positioning gains of the series of sample sound signals.

8. The method of claim 7, wherein weighting factors are used for calculating the weighted average which take into account at least one of the following variables:
a time sequence of the series of sample sound signals, wherein a weighting factor is attributed based on a temporal position within the series of sample sound signals;
environmental disturbances, wherein sample sound signals affected by the environmental disturbances are attributed proportionally lower weights; or
manipulations of the probe element by an operator, wherein sample sound signals affected by the manipulations are attributed proportionally lower weights.

9. The method of claim 1, wherein the statistical probability distribution is determined based on a linear discriminant analysis model, and the statistical probability distribution indicates a likelihood that the prediction distance equals each one of a range of predefined distance values from said tympanic membrane.

10. The method of claim 9, wherein the prediction distance is calculated as a weighted average of the predefined distance values, where the statistical probability distribution is used as a weight for each predefined distance value.

11. The method of claim 9, wherein a percentile of the statistical probability distribution is calculated to determine that a result is below a second measuring distance threshold value and, additionally to, or instead of, the condition of step f), only if the result is less than the second measuring distance threshold value, providing the information to the operator that the probe element is at the target position and performing the real ear measurement.

12. The method of claim 9, wherein the correction distance is calculated on the basis of the prediction distance, of the statistical probability distribution, and of at least one safety threshold designed to prevent the probe element from touching the tympanic membrane.

13. The method of claim 1, further comprising providing a feedback to the operator relating to the correction distance, in order to allow an adjustment of a position of the probe element according to the indication of the correction distance, wherein the feedback is at least one of tactile, acoustic, or visual.

14. A measuring system comprising:
   a probe element adapted to be inserted in an ear canal of an individual;
   a loudspeaker configured to deliver a sample sound signal to the ear canal;
   at least one microphone configured to detect a response to the sample sound signal;
   wherein the probe element is in acoustic communication with the loudspeaker and with the at least one microphone; and
   a signal processing unit for performing an acoustic measurement of a response to the sample sound signal, based on an electrical input signal from the at least one microphone, the measuring system being configured to perform a real ear measurement according to the method of claim 1.

15. The measuring system of claim 14, wherein the loudspeaker is one of external to the ear canal or is configured to be brought inside the ear canal by way of the probe element.

16. The measuring system of claim 14, wherein the probe element is calibrated to provide an operator with an indication of the regarding changes in adjustment of a position of the probe element.

\* \* \* \* \*